(12) United States Patent
Kim et al.

(10) Patent No.: US 10,428,372 B2
(45) Date of Patent: Oct. 1, 2019

(54) PROBE SYSTEM FOR REAL-TIME QUANTITATIVE AND QUALITATIVE ANALYSIS OF BIOMATERIAL, REACTION CHAMBER WITH SAID PROBE SYSTEM, AND ANALYSIS METHOD THEREOF

(71) Applicant: K-MAC BIO CENTER CORP., Cheongju-si (KR)

(72) Inventors: Lee Kyung Kim, Daejeon (KR); Mun Cheol Paek, Daejeon (KR); Su Jin Ku, Daejeon (KR); Sun Young Park, Daejeon (KR); Jong Pil Park, Seoul (KR); Do Bu Lee, Incheon (KR); Nam Joong Kim, Daejeon (KR); Jin Seok Noh, Daejeon (KR)

(73) Assignee: SUGENTECH, INC., Daejeon (KR)

( * ) Notice: Subject to any disclaimer, the term of this patent is extended or adjusted under 35 U.S.C. 154(b) by 71 days.

(21) Appl. No.: 15/531,352

(22) PCT Filed: Jan. 26, 2015

(86) PCT No.: PCT/KR2015/000817
§ 371 (c)(1),
(2) Date: May 26, 2017

(87) PCT Pub. No.: WO2016/085036
PCT Pub. Date: Jun. 2, 2016

(65) Prior Publication Data
US 2017/0327878 A1 Nov. 16, 2017

(30) Foreign Application Priority Data
Nov. 28, 2014 (KR) .................. 10-2014-0169104

(51) Int. Cl.
*C12Q 1/6837* (2018.01)
*C12Q 1/6823* (2018.01)
(Continued)

(52) U.S. Cl.
CPC ......... *C12Q 1/6837* (2013.01); *C12Q 1/6818* (2013.01); *C12Q 1/6823* (2013.01);
(Continued)

(58) Field of Classification Search
CPC ... C12Q 1/6837; C12Q 1/6818; C12Q 1/6825
See application file for complete search history.

(56) References Cited

U.S. PATENT DOCUMENTS

2003/0068629 A1* 4/2003 Rothberg ............. B01L 3/5027
435/6.12
2007/0035819 A1* 2/2007 Bahatt ................ G01N 21/0332
359/366

(Continued)

FOREIGN PATENT DOCUMENTS

| KR | 2010-0081539 A | 7/2010 |
|---|---|---|
| KR | 2013-0006477 A | 1/2013 |
| KR | 2014-0085710 A | 7/2014 |

OTHER PUBLICATIONS

International Search Report issued in PCT/KR2015/000817 dated Jul. 24, 2015 (2 pages).

(Continued)

*Primary Examiner* — Narayan K Bhat
(74) *Attorney, Agent, or Firm* — Osha Liang LLP

(57) ABSTRACT

A probe system for real-time quantitative and qualitative analysis of a biomaterial, and a reaction chamber with the probe system, and an analysis method thereof are provided. The probe system, which is included in the reaction chamber having an optically transmissive flat bottom surface and having a test sample accommodated therein, includes a target probe-reporter probe linker accommodated in the reaction chamber and including a target probe, which includes a sequence complementary to a target nucleic acid sequence to be detected, a first fluorophore and a first quencher, and a reporter probe linked to an end of the target (Continued)

probe and including a sequence non-complementary to the target nucleic acid sequence, and a capture probe included in a biochip formed on a bottom surface of the reaction chamber and including a complementary sequence hybridizable with the non-complementary sequence of the reporter probe, a second fluorophore and a second quencher.

6 Claims, 4 Drawing Sheets

(51) Int. Cl.
    *C12Q 1/6834*     (2018.01)
    *C12Q 1/6818*     (2018.01)
    *C12Q 1/6825*     (2018.01)
    *G01N 21/64*     (2006.01)

(52) U.S. Cl.
    CPC ......... *C12Q 1/6825* (2013.01); *C12Q 1/6834* (2013.01); *G01N 2021/6432* (2013.01)

(56) References Cited

U.S. PATENT DOCUMENTS

| | | | |
|---|---|---|---|
| 2009/0075273 A1* | 3/2009 | Dorn | G01N 21/6428 435/6.11 |
| 2012/0196283 A1 | 8/2012 | Babiel et al. | |
| 2013/0303390 A1 | 11/2013 | Seo et al. | |
| 2015/0031577 A1* | 1/2015 | Boissinot | C12Q 1/6823 506/9 |

OTHER PUBLICATIONS

Witten Opinion of the International Searching Authority issued in PCT/KR2015/000817 dated Jul. 24, 2015 (7 pages).
Korean Office Action in corresponding Application No. 10-2014-0169104 dated Jul. 22, 2016 (15 pages).
Arya, M. et al.; "Basic principles of real-time quantitative PCR"; Expert Rev. Mol. Diagn., vol. 5, No. 2, 2005, pp. 1-11 (11 pages).
Faltin, B. et al.; "Mediator Probe PCR: A Novel Approach for Detection of Real-Time PCR Based on Label-Free Primary Probes and Standardized Secondary Universal Fluorogenic Reporters"; Clinical Chemistry, vol. 58, No. 11, Jul. 27, 2012, pp. 1546-1556 (17 pages).
Faltin, B. et al.; "Current Methods for Fluorescence-Based Universal Sequence-Dependent Detection of Nucleic Acids in Homogenous Assays and Clinical Applications"; Clinical Chemistry, vol. 59, No. 11, Jul. 15, 2013, pp. 1567-1582 (16 pages).
Ramalingam, N. et al.; "Real-time PCR-based microfluidic array chip for simultaneous detection of multiple waterborne pathogens"; Sensors and Actuators B: Chemical, vol. 145, No. 1, 2010, pp. 543-552 (11 pages).
Livak, K.J. et al.; "Oligonucleotides with fluorescent dyes at opposite ends provide a quenched probe system useful for detecting PCR product and nucleic acid hybridization"; Genome Research, vol. 4, No. 6, Mar. 6, 1995, pp. 357-362 (8 pages).

* cited by examiner

[Fig. 1]
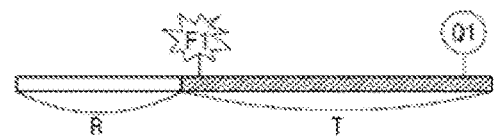
[Fig. 2]
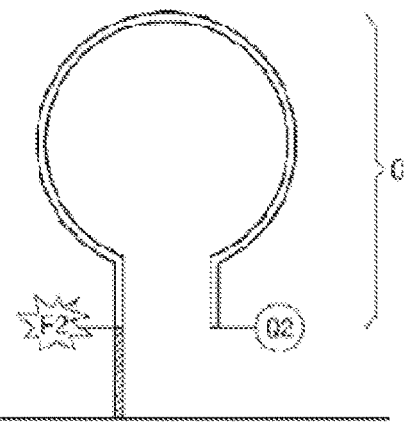
[Fig. 3]
[Fig. 4]
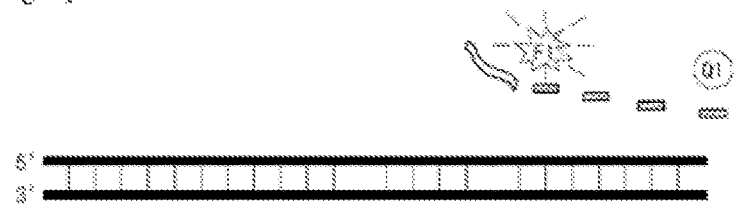
[Fig. 5]
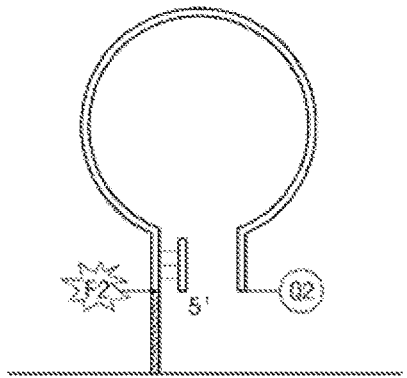

[Fig. 6]
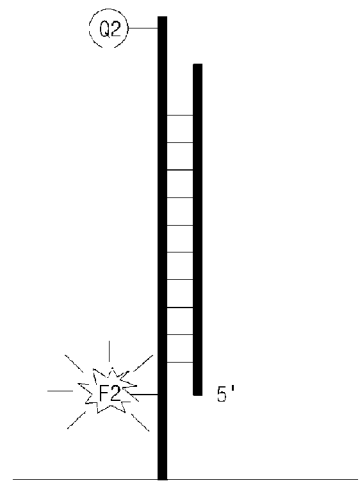
[Fig. 7]
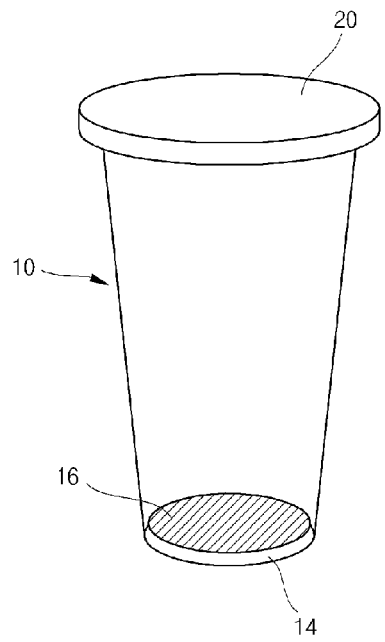

[Fig. 8]
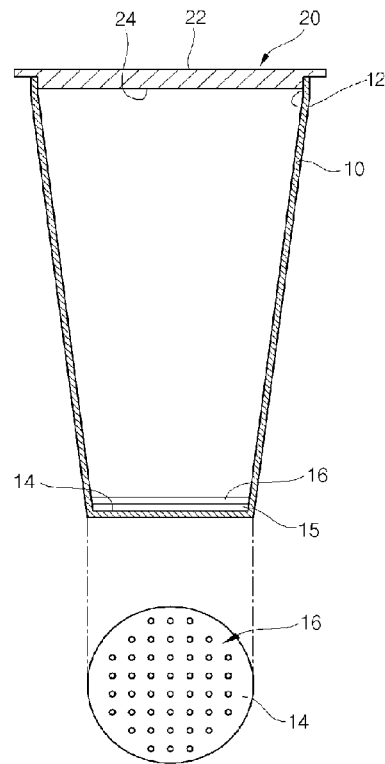
[Fig. 9]
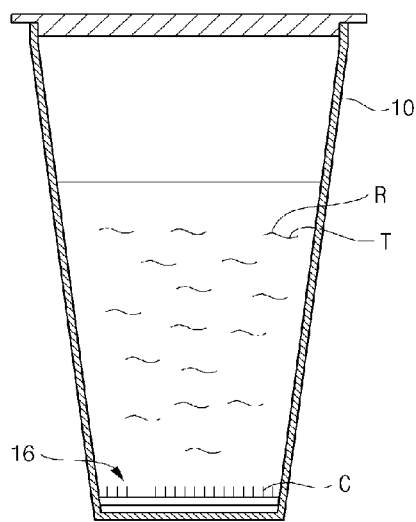

[Fig. 10]
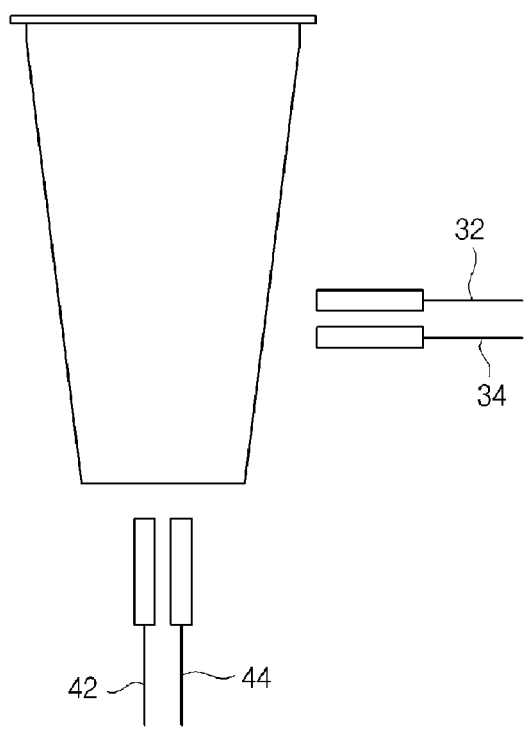

PROBE SYSTEM FOR REAL-TIME QUANTITATIVE AND QUALITATIVE ANALYSIS OF BIOMATERIAL, REACTION CHAMBER WITH SAID PROBE SYSTEM, AND ANALYSIS METHOD THEREOF

TECHNICAL FIELD

The present invention relates to a technique for analysis of a biomaterial, and more particularly, to a probe system for real-time quantitative and qualitative analysis of a biomaterial, a reaction chamber with the probe system, and an analysis method thereof.

BACKGROUND ART

In recent years, methods of testing a target gene of an analyte which have been widely performed for molecular diagnosis mainly include quantitative methods and qualitative methods.

A quantitative method is a method of relatively or absolutely measuring an expression level and a copy number of a target gene. On the other hand, a qualitative method is a method of determining the presence and genotype of a target gene.

A representative method for quantitative analysis is a method using a real-time polymerase chain reaction (PCR). The analytic methods using real-time PCR have been widely used since they have advantages in that quantitative analysis is possible, and that it is possible to reduce the risk of contamination by the air since genetically amplified signals are obtained without opening a tube after an analyte is mixed with a reagent. However, such methods have problems in that it is difficult to analyze six or more different types of analytes since a maximum of six fluorescent materials may be analyzed in one tube at the same time, and thus the analytes should be assigned to and tested in several tubes when there are several tens of genetic mutations and genotypes of the analytes to be tested.

A representative method for qualitative analysis is a method using a DNA microarray. The analytic method using a DNA microarray has an advantage in that one kind of fluorescence may be used to test various genotypes at a time since a number of target probes are fixed on a surface of one support, but has a limitation in that it is impossible to quantitatively analyze the genotypes.

DISCLOSURE OF INVENTION

Technical Problem

The present invention is directed to a probe system provided in a reaction chamber so that real-time quantitative and qualitative analysis of a biomaterial can be carried out in one reaction chamber without opening or washing the reaction chamber, a reaction chamber with the probe system, and an analysis method thereof.

Solution to Problem

According to an aspect of the present invention, there is provided a probe system for real-time quantitative and qualitative analysis of a biomaterial, which is included in a reaction chamber having an optically transmissive flat bottom surface and having a test sample accommodated therein. Here, the probe system includes a target probe-reporter probe linker accommodated in the reaction chamber and including a target probe, which has a sequence complementary to a target nucleic acid sequence to be detected and includes a first fluorophore and a first quencher, and a reporter probe linked to an end of the target probe and having a sequence non-complementary to the target nucleic acid sequence, and a capture probe included in a biochip formed on a bottom surface of the reaction chamber and having a complementary sequence hybridizable with the non-complementary sequence of the reporter probe and including a second fluorophore and a second quencher.

According to one exemplary embodiment of the present invention, the target probe-reporter probe linker may be designed so that the target probe is hybridized with target nucleic acids of a test sample, a first fluorescence signal is generated from the first fluorophore when the target probe is digested with a polymerase having nuclease activities, and the reporter probe is digested from the target probe with the polymerase having the nuclease activities to be released into the reaction chamber, and the capture probe may be hybridized with the reporter probe released into the solution in the reaction chamber, and the capture probe may be structurally changed by extended strands formed by hybridization with the reporter probe to emit a second fluorescence signal.

According to one exemplary embodiment of the present invention, the target probe-reporter probe linker may be designed so that a portion of the target probe is hybridized with the target nucleic acid sequence to form double strands when the target probe is hybridized with the target nucleic acids of the test sample, and a portion of the reporter probe is present in a single strand since the portion of the reporter probe is not hybridized with the target nucleic acid sequence, and may be designed so that a first fluorescence signal is generated while spacing the first quencher from the first fluorophore through the digestion of the target probe with the polymerase having the nuclease activities, and the digestion and release of the reporter probe from the target probe with the polymerase having the nuclease activities are induced, and the capture probe may be designed so that an extension reaction by the reporter probe hybridized with the capture probe occurs to form extended strands, and the capture probe is structurally changed by the extended strands so that a second fluorophore and a second quencher included in the capture probe are spaced apart to generate a second fluorescence signal from the second fluorophore.

According to one exemplary embodiment of the present invention, the capture probe may have a hairpin structure including a fluorophore and a quencher.

According to another aspect of the present invention, there is provided a reaction chamber for quantitative and qualitative analysis of a biomaterial, which has a top opening and a test sample accommodated therein and is hermetically closed with a cap installed at the opening after introduction of the test sample. Here, reaction chamber includes (a) an optically transmissive window formed at a bottom surface of the reaction chamber and having an optically transmissive flat surface formed therein, (b) a surface formed on the optically transmissive window to be modified with at least one functional group selected from the group consisting of amine, aldehyde, and epoxy functional groups, and (c) a biochip formed on the modified surface.

According to one exemplary embodiment of the present invention, the biochip may include a capture probe having a complementary sequence capable of hybridizing with the non-complementary sequence of the reporter probe, a fluorophore, and a quencher.

According to one exemplary embodiment of the present invention, the capture probe may be a probe having a hairpin structure including a fluorophore and a quencher.

According to one exemplary embodiment of the present invention, the reaction chamber may be in a cylindrical shape having a tapered lateral surface so that a diameter of a cross section increases from a lower portion to an upper portion thereof.

According to one exemplary embodiment of the present invention, the optically transmissive window of the reaction chamber may be formed of at least one material selected from the group consisting of glass, quartz, fumed silica, acryl, a poly-carbonate, a cyclic olefin copolymer (COC), and a cyclic olefin polymer (COP).

According to one exemplary embodiment of the present invention, the reaction chamber may be formed of at least one material selected from the group consisting of glass, quartz, fumed silica, acryl, a polycarbonate, a cyclic olefin copolymer (COC), and a cyclic olefin polymer (COP).

According to still another aspect of the present invention, there is provided a method for real-time quantitative and qualitative analysis of a biomaterial, which includes (a) introducing a test sample into a reaction chamber, (b) amplifying and hybridizing a gene, and (c) detecting first and second fluorescence signals.

According to one exemplary embodiment of the present invention, in the introducing of the test sample into the reaction chamber (operation (a)), the reaction chamber may have a top opening and a test sample accommodated therein and may be hermetically closed with a cap installed at the opening after introduction of the test sample. Here, a bottom surface of the reaction chamber may have an optically transmissive window having an optically transmissive flat surface formed therein, a biochip may be formed on the optically transmissive window, a target probe-reporter probe linker, which includes a target probe, which has a sequence complementary to a target nucleic acid sequence to be detected and includes a first fluorophore and a first quencher, and a reporter probe linked to an end of the target probe and having a sequence non-complementary to the target nucleic acid sequence, may be accommodated in the reaction chamber, and the biochip may include a capture probe having a complementary sequence capable of hybridizing with the non-complementary sequence of the reporter probe, and a second fluorophore, and a second quencher.

According to one exemplary embodiment of the present invention, in the amplifying and hybridizing of the gene (operation (b)), when the target probe is hybridized with target nucleic acids of a test sample, a first fluorescence signal may be generated from the first fluorophore of the target probe while the target probe is digested with a polymerase having nuclease activities, the reporter probe may be digested from the target probe with the polymerase having the nuclease activities to be released into the reaction chamber, and the capture probe may be hybridized with the reporter probe released into the reaction chamber to emit a second fluorescence signal due to a structural change of the capture probe caused by an extension reaction.

According to one exemplary embodiment of the present invention, in the detection of the first and second fluorescence signals (operation (c)), quantitative analysis of the target nucleic acids from the first fluorescence signal may be performed, and qualitative analysis of the target nucleic acids from the second fluorescence signal may be performed.

According to one exemplary embodiment of the present invention, the amplifying and hybridizing of the gene may include i) hybridizing a portion of the target probe with the target nucleic acid sequence in the target probe-reporter probe linker to form double strands and not hybridizing of a portion of the reporter probe with the target nucleic acid sequence so that the portion of the reporter probe is present in a single strand, ii) inducing digestion of the target probe and the reporter probe with the polymerase having the nuclease activities so that the first fluorophore and the first quencher of the target probe are spaced apart to generate a first fluorescence signal, and releasing the reporter probe into the reaction chamber, iii) hybridizing the released reporter probe with the capture probe included in the biochip, and iv) allowing an extension reaction to occur by the reporter probe hybridized with the capture probe to form extended strands, and allowing the extended strands to structurally change the capture probe so that the second fluorophore and the second quencher included in the capture probe are spaced apart to generate a second fluorescence signal from the second fluorophore.

According to one exemplary embodiment of the present invention, the detection of the first fluorescence signal and the second fluorescence signal may be directly performed in the reaction chamber in which the amplification and hybridization of the gene are completed.

According to one exemplary embodiment of the present invention, the first fluorescence signal and the second fluorescence signal may have different wavelengths.

According to one exemplary embodiment of the present invention, the first fluorescence signal may be generated from a plurality of materials having different wavelengths.

Advantageous Effects of Invention

According to one exemplary embodiment of the present invention, real-time PCR and a DNA chip reaction can be performed together in one reaction chamber, and it is possible to detect signals for qualitative and quantitative analysis in situ without transferring the reaction chamber when a reaction is completed.

Particularly, according to one exemplary embodiment of the present invention, since PCR reaction and DNA chip signals can be obtained in real time in the reaction chamber, the quantitative and qualitative analysis is possible without opening or washing the chamber, and it is also possible to perform quantitative analyses and genotype tests in economical and reliable manner at the same time in various fields of molecular diagnoses, such as drug resistance, somatic mutation, and single nucleotide polymorphism, as well as examination of infectious diseases.

Therefore, the method for real-time quantitative and qualitative analysis of a biomaterial according to one exemplary embodiment of the present invention can be easily used in the whole field of molecular diagnoses regardless of the types of tests such as quantitative analysis, genotype tests, etc.

BRIEF DESCRIPTION OF DRAWINGS

FIG. 1 is a diagram showing a target probe T-reporter probe R linker according to one exemplary embodiment of the present invention (F1: first fluorophore, and Q1: first quencher).

FIG. 2 is a diagram showing a capture probe C according to one exemplary embodiment of the present invention (F2: second fluorophore, and Q2: second quencher).

FIGS. 3 to 6 are diagrams for describing generation of a fluorescence signal and detection of target nucleic acids using a probe system according to one exemplary embodiment of the present invention.

FIG. 7 is a perspective view of a reaction chamber for real-time quantitative and qualitative analysis of a biomaterial according to one exemplary embodiment of the present invention.

FIG. 8 is a cross-sectional view of the reaction chamber for real-time quantitative and qualitative analysis of a biomaterial according to one exemplary embodiment of the present invention.

FIG. 9 is a diagram for describing a test sample introduced into the reaction chamber for real-time quantitative and qualitative analysis of a biomaterial according to one exemplary embodiment of the present invention.

FIG. 10 is a diagram for describing one exemplary embodiment of a light source and a detector used for real-time quantitative and qualitative analysis of a biomaterial according to one exemplary embodiment of the present invention.

BEST MODE FOR CARRYING OUT THE INVENTION

Hereinafter, preferred embodiments of the present invention will be described in detail with reference to the accompanying drawings. However, it should be understood that changes and modifications may be made in these embodiments without departing from the scope of the invention. Therefore, it would be appreciated by those skilled in the art that the detailed description disclosed herein is merely representative for purposes of fully describing exemplary embodiments of the present invention and providing the scope of the present invention to those skilled in the related art to which the present invention belongs, and is defined in the claims and their equivalents.

Hereinafter, the present invention will be described in detail with reference to the accompanying drawings.

FIG. 1 is a diagram showing a target probe T-reporter probe R linker according to one exemplary embodiment of the present invention (F1: first fluorophore, and Q1: first quencher), and FIG. 2 is a diagram showing a capture probe C according to one exemplary embodiment of the present invention (F2: second fluorophore, and Q2: second quencher).

The probe system according to one exemplary embodiment of the present invention includes a target probe T-reporter probe R linker, and a capture probe C.

The target probe T-reporter probe R linker is formed by linking a target probe T to a reporter probe R.

The target probe T has a sequence complementary to a target nucleic acid sequence to be detected, a first fluorophore F1, and a first quencher Q1. The reporter probe R is linked to an end of the target probe, and has a sequence non-complementary to the target nucleic acid sequence to be detected. According to one exemplary embodiment of the present invention, the target probe T-reporter probe R linker is provided while the target probe T-reporter probe R linker is accommodated in a reaction chamber 10, or introduced into the reaction chamber together with a test sample and a reagent.

The capture probe C has a complementary sequence capable of hybridizing with the non-complementary sequence of the reporter probe, and includes a second fluorophore F2 and a second quencher Q2. According to one exemplary embodiment of the present invention, the capture probe C is included in a biochip formed on a bottom surface 14 of the reaction chamber 10.

According to one exemplary embodiment of the present invention, a probe hybridized with target nucleic acids of a test sample is the target probe T. Also, the reporter probe R may be linked to an end of the target probe T to form a linker. When the reporter probe R is digested and released from the target probe T, the reporter probe R is hybridized with the capture probe C.

The target probe T and the capture probe C is in a quenched state before hybridization since a fluorophore and quencher are present in the form of a molecular beacon. Therefore, fluorescence may be generated only from the hybridized probe, thereby reducing background signals.

The target probe T may form double strands with target nucleic acids of the test sample since the target probe T has a sequence complementary to the target nucleic acids of the test sample, and the reporter probe R forming a linker with the target probe T is present in a single strand even when the target probe is hybridized with the target nucleic acids since the reporter probe R has a sequence non-complementary to the target nucleic acids. When the target probe T is digested by a polymerase having nuclease activities after the target probe T is hybridized with the target nucleic acids, the reporter probe R linked to the target probe T is also released into a reaction solution. Then, when the target probe T is digested by the polymerase having nuclease activities, the first fluorophore F1 of the target probe T is spaced apart from the first quencher Q1 to generate a first fluorescence signal.

The reporter probe R has a sequence complementary to the capture probe C. Thus, the reporter probe R is released into the reaction solution, and then hybridized with the capture probe C. The reporter probe R is hybridized with the capture probe C to serve as a primer. In this case, the second fluorophore and the second quencher included in the form of a molecular beacon in the capture probe are spaced from each other while a structure of the capture probe is unfolded by the extended strands extending from the reporter probe R, thereby generating a second fluorescence signal.

The capture probe is preferably a probe having a hairpin structure including a fluorophore and a quencher.

FIGS. 3 to 6 are diagrams for describing in detail generation of a fluorescence signal and detection of target nucleic acids using a probe system according to one exemplary embodiment of the present invention.

Referring to FIGS. 3 to 6, when an amplification and hybridization reaction is initiated, an amplification primer and a target probe T-reporter probe R linker are linked to each complementary sequence region of the target nucleic acids (FIG. 3). An extension reaction is initiated from the amplification primer, and the hybridized target probe T is digested with a polymerase having nuclease activities (FIG. 4). A first fluorophore released upon digestion of the target probe is spaced apart from a first quencher to generate a first fluorescence signal (FIG. 4). The polymerase having the nuclease activities digests all the target probe T to be released, and the reporter probe R dangled from an end of the target probe T is also released into a reaction solution (FIG. 4). The released reporter probe R is hybridized with a complementary sequence region of the capture probe C included in a biochip (FIG. 5). The hybridized reporter probe R serves as a primer to initiate an extension reaction (FIG. 5). The extended strands of the reporter probe R unfolds a structure of the capture probe C so that a second fluorophore and a second quencher included in the capture probe C are spaced apart to generate a second fluorescence signal (FIG. 6).

When different types of the first fluorophore F1 are linked according to the sequence of the target probe T, quantitative analysis of each sequence is possible. Generally, 4 to 6 types of target nucleic acid sequences may be quantified in one reaction chamber in the case of apparatuses currently known in the related art. In the method according to one exemplary embodiment of the present invention, however, a larger number of target nucleic acids may be quantified due to increased specificity of probe systems and high detection sensitivity of fluorescence signals. The number of the types of nucleic acid sequences detectable according to the performance of the apparatus may vary. Also, when the same fluorescent material is used for a large number of types of target probes, a limited number of real-time PCR detectors may be used to sufficiently detect fluorescence signals.

According to one exemplary embodiment of the present invention, a biochip in which different sequences of target nucleic acids are implanted at different sites is formed on a bottom surface of the reaction chamber. In this case, the capture probe C is linked to an end of the target nucleic acid sequence. Qualitative analysis of the target nucleic acids is possible, depending on whether a second fluorescence signal of the capture probe C is generated or not at each region. Various nucleic acid sequences of a target to be detected are attached to the biochip, and the capture probe is linked to an end of the nucleic acid sequence.

The first fluorescence signal and the second fluorescence signal are fluorescence signals having different wavelengths. Also, the first fluorescence signal may be generated from a plurality of materials having different wavelengths.

At least one material selected from the group consisting of pyrene, Cyanine 2, GFP, calcein, FITC, Alexa 488, FAM, fluorescein chlorotriazinyl, fluorescein, rhodamine 110, Oregon Green, Magnesium Green, Calcium Green, JOE, Cyanine 3, tetramethyl-rhodamine, TRITC, TAMRA, rhodamine phalloidin, Pyronin Y, Lissamine, ROX, Calcium Crimson, Texas Red, Nile Red, Cyanine 5, and thiadicarbocyanine may be used as the fluorescent material of the probe.

FIGS. 7 and 8 are diagrams for describing a reaction chamber with the probe system according to one exemplary embodiment of the present invention.

Referring to FIGS. 7 and 8, the reaction chamber 10 according to one exemplary embodiment of the present invention has a top opening 12 and can accommodate a test sample therein. Here, the opening 12 may be hermetically closed with a cap 20.

The reaction chamber 10 according to one exemplary embodiment of the present invention has a flat bottom surface 14, and is formed in a cylindrical shape having a tapered lateral surface so that a diameter of a cross section increases from a lower portion to an upper portion thereof. Since the reaction chamber 10 is easily installed and uninstalled in/from a reaction chamber accommodation unit of an analysis device configured to accommodate the reaction chamber since the lateral surface of the reaction chamber 10 has a tapered shape. In particular, since the reaction chamber 10 has a tapered lateral surface, the reaction chamber 10 may be easily uninstalled even when the reaction chamber 10 is thermally deformed due to repeated increase and decrease in temperature during a PCR procedure. Also, the cylindrical reaction chamber 10 having a tapered lateral surface enables more uniform heat transfer than chambers having polygonal cross sections, thereby improving heat conductivity during the PCR procedure.

According to one exemplary embodiment of the present invention, at least the bottom surface 14 of the reaction chamber 10 may be formed of an optically transmissive material having a light transmissivity of 50% or more to form an optically transmissive window, and the whole reaction chamber 10 may be formed of the same material.

Since the bottom surface of the reaction chamber 10 forms an optically transmissive window having a flat bottom surface, scattering of light may be minimized upon detection of fluorescence signals, thereby improving detection sensitivity.

Also, the flat bottom surface 14 is favorable to form a biochip.

According to one exemplary embodiment of the present invention, a modified surface 15 is formed on the bottom surface 14, and a biochip 16 in the form of a microarray is formed on the modified surface 15.

The modified surface 15 is formed by functionalizing the bottom surface 14 of the reaction chamber 10 with at least one selected from the group consisting of an amine group, an aldehyde group, and an epoxy group.

When DNA fragments are implanted in respective regions to form a biochip on the bottom surface 14 of the reaction chamber 10, the DNA fragments should be easily bound onto the bottom surface 14 of the reaction chamber 10. According to one exemplary embodiment of the present invention, the biochip 16 may be easily formed by forming the modified surface 15, which is functionalized with at least one selected from amine, aldehyde, and epoxy groups, on the bottom surface 14 of the reaction chamber 10. Therefore, the bottom surface 14 of the reaction chamber is characterized in that it is made of a material whose surface may be modified by easily functionalizing the surface with the amine, aldehyde, or epoxy functional group.

According to one exemplary embodiment of the present invention, the bottom surface of the reaction chamber 10 forms an optically transmissive window, and is formed of at least one material selected from the group consisting of glass, quartz, fumed silica, acryl, a polycarbonate, a cyclic olefin copolymer (COC), and a cyclic olefin polymer (COP) so that the bottom surface can be modified by easily functionalizing a surface of the material with the amine, aldehyde, or epoxy functional group.

The microarray-type biochip 16 in which different sequences of target nucleic acids are divided into certain regions and implanted in plural numbers is formed on the modified surface 15 formed on the bottom surface 14 of the reaction chamber 10, and the capture probe C is linked to ends of the target nucleic acids of the biochip. Therefore, the qualitative analysis of the target nucleic acids is possible, depending on whether a second fluorescence signal of the capture probe C is generated or not at each region.

According to one exemplary embodiment of the present invention, the opening 12 of the reaction chamber 10 is hermetically closed with the cap 20. The cap 20 may be optically transmissively formed of the same material as the reaction chamber 10.

In the analysis device accommodating the reaction chamber 10 according to one exemplary embodiment of the present invention, when light sources and detectors for detection of fluorescence signals are installed under the reaction chamber 10, the shape of the cap 20 need not be particularly limited. But, when the light sources and detectors are installed above the reaction chamber 10, or respectively installed above and under the reaction chamber 10, the cap 20 is optically transmissively formed, and a top surface 22 and a bottom surface 24 of the cap 20 are formed as flat surfaces to prevent scattering of light.

In the present invention, installing of the light sources and detectors above or under the reaction chamber 10 means that a path of light or fluorescence signals for detection of fluorescence signals are formed in upward and downward directions of the reaction chamber 10. Therefore, it is possible that the light sources and detectors are installed at different positions so that the paths of the light and fluorescence signals is changed in the upward and downward directions of the reaction chamber 10 by means of a lens, a mirror, etc.

FIG. 9 is a diagram for describing a test sample introduced into the reaction chamber according to one exemplary embodiment of the present invention.

The reaction chamber 10 according to one exemplary embodiment of the present invention accommodates a target probe T-reporter probe R linker Such a target probe T-reporter probe R linker is provided in a state in which the target probe T-reporter probe R linker may be introduced into the reaction chamber 10, or may be introduced upon introduction of a test sample.

Also, the present invention provides a method for real-time quantitative and qualitative analysis of a biomaterial, which includes (a) introducing a test sample into a reaction chamber, (b) amplifying and hybridizing a gene, and (c) detecting first and second fluorescence signals generated during a hybridization reaction.

In the introducing of the test sample into the reaction chamber (operation (a)), a test sample and a reagent are added to the reaction chamber 10, and the opening 12 is hermetically closed with the cap 20. An amplification primer and a PCR reagent are added together with the test sample. The test sample and the PCR reagent are mixed to prepare a reaction solution. The target-reporter probe according to one exemplary embodiment of the present invention may be added in a state in which the target-reporter probe is included in the PCR reagent, or may be included in a dried state in the reaction chamber before introduction of the test sample and the reagent.

As described above, the amplifying and hybridizing of the gene (operation (b)) is performed in a state in which the reaction solution is added and the body of the reaction chamber is hermetically closed with the cap.

The amplification of the gene is carried out in the same manner as in real-time PCR widely known in the related art.

The analysis device (not shown) configured to accommodate the reaction chamber has a heating block configured to apply heat to amplify the target nucleic acids. A real-time PCR procedure is performed with repeated increase and decrease in temperature due to an action of the heating block.

In the analysis device configured to accommodate the reaction chamber according to one exemplary embodiment of the present invention, a reaction chamber accommodation unit is preferably formed so that the heating block is disposed at a lateral surface of the reaction chamber accommodated in the analysis device.

The target nucleic acids are amplified by the amplification primer added with the repeated increase and decrease in temperature. Annealing and extension reaction by the amplification primer occur, the target probe hybridized with the target nucleic acids due to the extended strands is digested into fragments, and the reporter probe is also digested and released. The first fluorophore spaced apart from the first quencher generates a first fluorescence signal with digestion of the target probe. The first fluorescence signal emits fluorescence using a first light source, and is detected in real time by a first detector to quantitatively analyze a target gene.

A hybridization reaction in which the released reporter probe binds to the capture probe having a sequence complementary to the reporter probe occurs. In this case, the reporter probe serves as a primer to perform an extension reaction. The second fluorophore grows away from the second quencher while a structure of the capture probe is unfolded by the hybridization and extension, thereby generating a second fluorescence signal. The second fluorescence signal emits fluorescence using a second light source, and is detected by a second detector to quantitatively analyze a target gene.

The qualitative analysis using the second light source may be performed simultaneously with the quantitative analysis using the first light source, but is preferably performed after the quantitative analysis using the first light source. The quantitative analysis and the qualitative analysis may be performed in the same manner as in conventional real-time PCR and detection of the biochip.

The detection of the first fluorescence signal and the second fluorescence signal may be directly performed without washing or transferring the reaction chamber in which the amplification and hybridization of the gene is completed. In the prior art, only the first fluorescence signal is detected in the reaction chamber, and the reaction chamber is washed, and then transferred to another detector to detect a second fluorescence signal. In this case, it may be difficult to accurately detect the second fluorescence signal due to the contact with foreign substances such as the air. In the present invention, however, since the reporter probe is applied together with the target probe and the material and shape of the reaction chamber are newly designed, it is possible to perform the quantitative and qualitative analysis in real time without washing or transferring the reaction chamber when the reaction is completed. Also, since the contact with the foreign substances such as the air may be inhibited, detection reliability and convenience may be improved.

FIG. 10 is a diagram for describing one exemplary embodiment of a light source and a detector used for real-time quantitative and qualitative analysis of a biomaterial according to the present invention.

Referring to FIG. 10, a first light source 32 and a first detector 34 used to detect the first fluorescence signal generated as a result of the real-time PCR are arranged at a lateral surface of the reaction chamber 10, and a second light source 42 and a second detector 44 used to detect the second fluorescence signal in a biochip formed on a bottom surface of the reaction chamber are disposed under the reaction chamber 10. Since the bottom surface of the reaction chamber 10 is formed as a flat optically transmissive window, scattering of light may be minimized, thereby making it possible to enhance detection sensitivity.

According to a modified embodiment of the present invention, the first light source 32 and the first detector 34 used to detect the first fluorescence signal generated as a result of the real-time PCR may be formed on any surface of the reaction chamber. Also, the second light source 42 and the second detector 44 used to detect the second fluorescence signal in the biochip formed on the bottom surface of the reaction chamber may be installed above and under the reaction chamber 10 without limitation.

According to one exemplary embodiment of the present invention, the detection and analysis of the fluorescence signals may be performed using various methods. For example, the probe system may include at least one laser module (i.e., a light source), at least one expander module, an emission filter unit, an imaging lens, and a CCD camera (i.e., a detector) to detect and analyze the fluorescence signals.

The laser module is used to irradiate the reaction chamber with light. The expander module serves to adjust a refractive index of light so as to accurately irradiate the reaction chamber with light emitted from the laser module. The expander module is disposed at one side of the laser module, and includes a first lens and a second lens. The first lens serves to focus light emitted from the laser module and describe Gaussian distribution characteristics. The second lens serves to improve parallelism and uniformity of light focused by the first lens and output the light with a desired spot size. The emission filter unit serves to filter fluorescence expressed from a fluorescent material when the reaction chamber is irradiated with light. When the fluorescent material is irradiated with light with certain wavelengths from a light source, light with certain wavelengths innate to the corresponding material is expressed. In this case, the emission filter serves to filter light with wavelengths other than the certain wavelengths. The imaging lens serves to form an image for the fluorescence signal filtered from the emission filter unit on the CCD camera. The CCD camera serves to convert the fluorescence signal emitted from the imaging lens into a digital signal for image processing.

One exemplary embodiment of the present invention will be described.

First, a *Mycobacterium* amplification primer, a target probe-reporter probe linker for real-time PCR to differentiate *Mycobacterium* tuberculosis/nontuberculous *Mycobacterium* strains, and a capture probe for differentiating a nontuberculous *Mycobacterium* genotype are constructed. The *Mycobacterium* amplification primer is a primer capable of specifically amplifying only *Mycobacterium* sp., and all the *Mycobacterium* tuberculosis/nontuberculous *Mycobacterium* strains belonging to the *Mycobacterium* sp. may be detected by the primer without distinction.

For real-time quantification (real-time PCR) of the *Mycobacterium* tuberculosis and nontuberculous *Mycobacterium* strains, a target probe-reporter probe linker is constructed, and a portion of the target probe has a complementary base sequence specific to a base sequence of each targeted nucleic acids, and the reporter probe linked to the target probe has any non-complementary sequence regardless of the target nucleic acids, and is constructed as a base sequence complementary to each capture probe. For real-time quantification of the *Mycobacterium* tuberculosis strains, FAM and BHQ1 are attached as a fluorophore and a quencher, respectively, to both ends of the target probe. For real-time quantification of the nontuberculous *Mycobacterium* strains, Cy5 and BHQ1 are commonly attached as the fluorophore and the quencher, respectively, to both ends of the target probe. Therefore, the target probe is constructed so that the FAM and Cy5 wavelengths can be detected when the *Mycobacterium* tuberculosis and nontuberculous *Mycobacterium* strains are present, respectively.

The capture probe for differentiating a nontuberculous *Mycobacterium* genotype has a base sequence complementary to a base sequence of the reporter probe, and consists of any base sequence regardless of the base sequence of the target nucleic acids. In this case, the capture probe is constructed to attach a Cy3 fluorescent material and a BHQ1 quenching material and form a hairpin structure. A sequence of a hairpin structure in which the capture probe is linked to a gene sequence of each nontuberculous *Mycobacterium* strain is constructed so that the sequence of the hairpin structure is fixed in a flat bottom surface of the reaction chamber in advance to form a biochip, and the digested and released reporter probe during a gene amplification procedure reacts with the capture probe for differentiating a nontuberculous *Mycobacterium* genotype to emit signals.

The manufacture of the reaction chamber and the biochip are as described below.

A 200 µl tube having a flat bottom surface is manufactured using a cyclic olefin copolymer (COC) (FIG. 7). The flat bottom surface of the tube is modified by functionalizing the bottom surface with an amine. Each of the constructed capture probe for differentiating a nontuberculous *Mycobacterium* genotype is diluted to a concentration of 100 pmol, and a spotting solution is added thereto to a concentration of 50 pmol, and thoroughly mixed. Thereafter, the capture probe is attached to the amine-modified bottom surface of the tube using a microarray. To remove the probe which is not attached to a surface of a support, the tube is washed with a 0.2% sodium dodecyl sulfate (SDS) solution at room temperature, and then washed with distilled water. The tube is washed with a sodium borohydride solution, and completely dried using a centrifuge to complete the manufacture of a microarray (i.e., a biochip).

The presence of the *Mycobacterium* tuberculosis and nontuberculous *Mycobacterium* strains is determined and the detection of the nontuberculous *Mycobacterium* genotype is performed, as follows.

The manufactured *Mycobacterium* amplification primer, a real-time gene-amplifying reagent including the target probe-reporter probe linker for real-time quantification (real-time PCR) of the *Mycobacterium* tuberculosis and nontuberculous *Mycobacterium* strains, and target nucleic acids are added at desired amounts to the tube having the flat bottom surface in which the constructed capture probe is fixed. Thereafter, a real-time PCR and hybridization reaction is carried out. FAM and Cy5 fluorescence signals generated in the tube during a gene amplification procedure are obtained in real time by a camera to obtain a quantitative analytic value. When the reaction is completed, the Cy3 fluorescence signal reacting with the probe is obtained by a fluorescence detector to perform qualitative analysis of a DNA chip.

While the invention has been shown and described with reference to certain exemplary embodiments thereof, it will be understood by those skilled in the art that various changes in form and details may be made therein without departing from the scope of the invention as defined by the appended claims.

The invention claimed is:

1. A method for real-time quantitative and qualitative analysis of a biomaterial, comprising:
   (a) introducing a test sample into a reaction chamber, wherein the reaction chamber has a top opening and the test sample accommodated therein and is hermetically closed with a cap installed at the opening after introduction of the test sample, wherein a bottom surface of the reaction chamber comprises an optically transmissive window having an optically transmissive flat surface; a biochip is formed on the optically transmissive window; a target probe-reporter probe linker, which comprises a target probe, which has a sequence complementary to a target nucleic acid sequence to be detected, and comprises a first fluorophore and a first quencher, and a reporter probe linked to an end of the target probe and having a sequence non-complementary to the target nucleic acid sequence, is accommodated in the reaction chamber; and the biochip comprises a capture probe having a complementary sequence capable of hybridizing with the non-complementary sequence of the reporter probe and comprising a second fluorophore and a second quencher;

(b) hybridizing and amplifying, wherein, when the target probe is hybridized with target nucleic acids of the test sample, a first fluorescence signal is generated from the first fluorophore of the target probe while the target probe is digested with a polymerase having nuclease activities, the reporter probe is digested from the target probe with the polymerase having the nuclease activities to be released into the reaction chamber, and the capture probe having the complementary sequence is hybridized with the non-complimentary sequence of the reporter probe released into the reaction chamber to emit a second fluorescence signal due to a structural change of the capture probe caused by an extension reaction; and (c) detecting the first and second fluorescence signals, wherein quantitative analysis of the target nucleic acids from the first fluorescence signal is performed, and qualitative analysis of the target nucleic acids from the second fluorescence signal is performed.

2. The method of claim 1, wherein the hybridizing and amplifying comprises:

i) hybridizing a portion of the target probe with the target nucleic acid sequence in the target probe-reporter probe linker to form double strands and not hybridizing a portion of the reporter probe with the target nucleic acid sequence so that the portion of the reporter probe is present in a single strand;

ii) inducing digestion of the target probe and the reporter probe with the polymerase having the nuclease activities so that the first fluorophore and the first quencher of the target probe are spaced apart to generate a first fluorescence signal, and releasing the reporter probe into the reaction chamber;

iii) hybridizing the released reporter probe with the capture probe included in the biochip; and iv) allowing an extension reaction to occur by the non-complimentary sequence of the reporter probe hybridized with the complimentary sequence of the capture probe to form extended strands, and allowing the extended strands to structurally change the capture probe so that the second fluorophore and the second quencher included in the capture probe are spaced apart to generate a second fluorescence signal from the second fluorophore.

3. The method of claim 1, wherein the detection of the first fluorescence signal and the second fluorescence signal is directly performed in the reaction chamber in which the amplification and hybridization of the gene are completed.

4. The method of claim 1, wherein the first fluorescence signal and the second fluorescence signal have different wavelengths.

5. The method of claim 1, wherein the first fluorescence signal is generated from a plurality of fluorescent materials having different wavelengths.

6. The method of claim 1, wherein a second light source radiated to the second fluorophore and a second detector configured to detect the second fluorescence signal are disposed above or under the reaction chamber.

* * * * *